(12) United States Patent
Moser et al.

(10) Patent No.: US 11,717,369 B2
(45) Date of Patent: Aug. 8, 2023

(54) EXTERNAL ACTUATION DEVICE FOR ADJUSTABLE IMPLANTED MEDICAL DEVICE

(71) Applicants: Yves Moser, Yverdon-les-Bains (CH); David Wayne Daniels, Winona Lake, IN (US)

(72) Inventors: Yves Moser, Yverdon-les-Bains (CH); David Wayne Daniels, Winona Lake, IN (US)

( * ) Notice: Subject to any disclaimer, the term of this patent is extended or adjusted under 35 U.S.C. 154(b) by 187 days.

(21) Appl. No.: 16/899,263

(22) Filed: Jun. 11, 2020

(65) Prior Publication Data

US 2020/0390509 A1  Dec. 17, 2020

Related U.S. Application Data

(60) Provisional application No. 62/860,061, filed on Jun. 11, 2019.

(51) Int. Cl.
| | |
|---|---|
| *A61B 34/00* | (2016.01) |
| *H01F 7/02* | (2006.01) |
| *A61B 17/70* | (2006.01) |
| *A61B 90/00* | (2016.01) |

(52) U.S. Cl.
CPC ........... *A61B 34/73* (2016.02); *H01F 7/0242* (2013.01); *A61B 17/7016* (2013.01); *A61B 2034/733* (2016.02); *A61B 2090/064* (2016.02)

(58) Field of Classification Search
CPC ............... A61B 34/73; A61B 17/7016; A61B 2034/733; A61B 2090/064; H01F 7/0242
See application file for complete search history.

(56) References Cited

U.S. PATENT DOCUMENTS

| | | |
|---|---|---|
| 7,862,502 B2 | 1/2011 | Pool et al. |
| 9,078,711 B2 | 7/2015 | Quick |
| 2012/0035656 A1 | 2/2012 | Pool et al. |
| 2014/0031870 A1 | 1/2014 | Chang et al. |
| 2016/0113683 A1 | 4/2016 | Cheng |

FOREIGN PATENT DOCUMENTS

WO   2008109300 A2   9/2008

OTHER PUBLICATIONS

Young, Lee; International Search Report and Written Opinion of the International Searching Authority, issued in International Application No. PCT/US2020/037271; dated Sep. 17, 2020; 8 pages.

Filali, Salima; European Extended Search Report, issued in EP Application No. 20821944; dated May 3, 2023; 10 pages.

*Primary Examiner* — Mohamad A Musleh
(74) *Attorney, Agent, or Firm* — Ulmer & Berne LLP

(57) ABSTRACT

An external actuation device includes a housing, a motor, a driving magnet, a sensor, and a controller. The motor includes a driveshaft that is rotatable about a rotation axis. The driving magnet is rotatably coupled with the driveshaft and is rotatable together with the driveshaft about the rotation axis. The sensor is associated with the driving magnet and is configured to detect a magnetic force between the driving magnet and a driven magnet disposed adjacent to the driving magnet. The controller is in communication with the motor and the sensor.

19 Claims, 7 Drawing Sheets

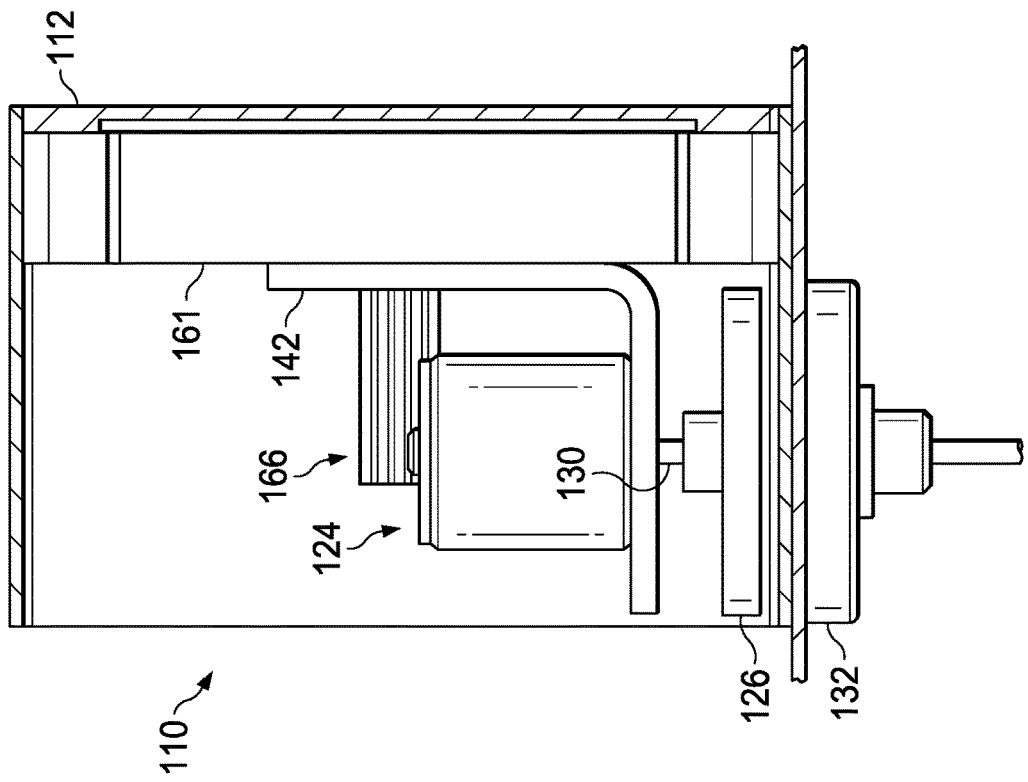
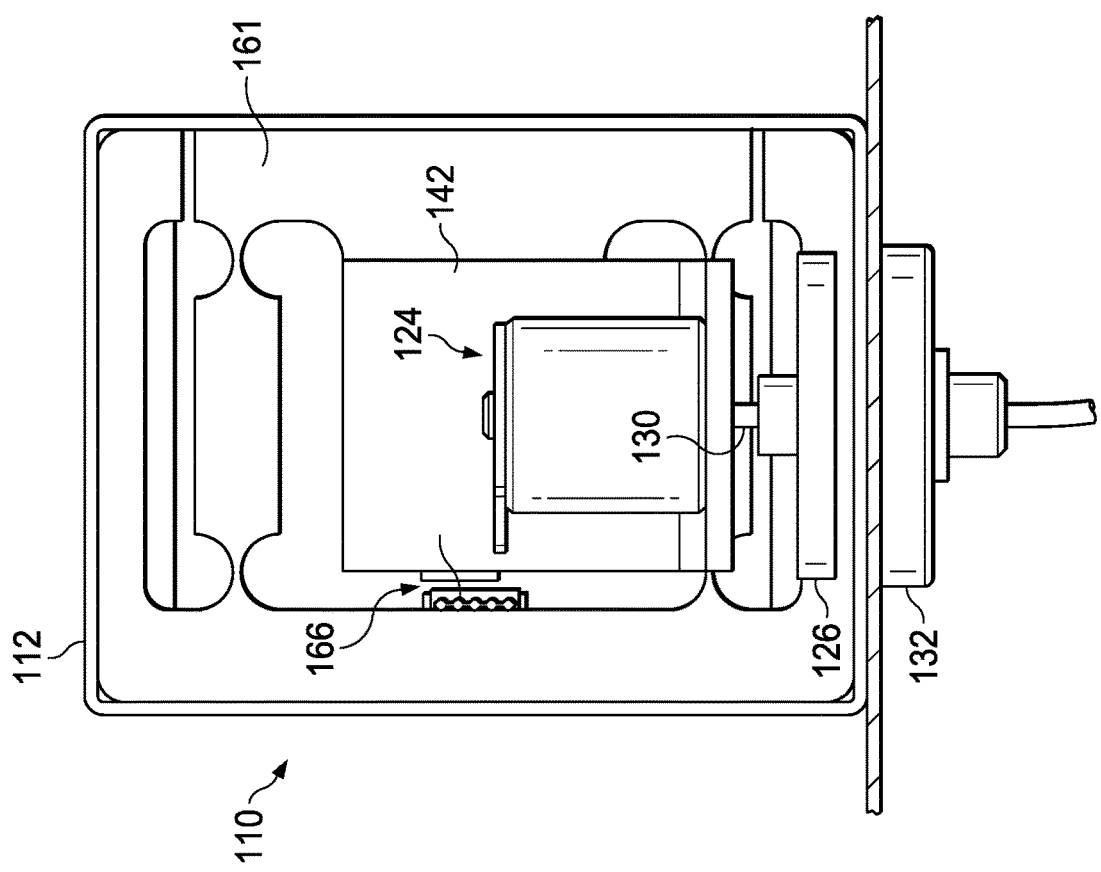
FIG. 7
FIG. 8

EXTERNAL ACTUATION DEVICE FOR ADJUSTABLE IMPLANTED MEDICAL DEVICE

REFERENCE TO RELATED APPLICATION

This application claims priority of U.S. provisional patent application Ser. No. 62/860,061, entitled External Actuation Device for Adjustable Implanted Medical Device, filed Jun. 11, 2019, and hereby incorporates this provisional patent application by reference herein in its entirety.

TECHNICAL FIELD

The apparatus described below generally relates to an external actuation device for an adjustable implanted medical device. In particular, the actuation device includes a driving magnet that interacts with a driven magnet of the adjustable implanted medical device to facilitate lengthening of the device.

BACKGROUND

Some adjustable implanted medical devices, such as a distraction rod, a growing rod, or a restriction collar, are associated with a driven magnet that can be rotated to facilitate adjustment of the adjustable implanted medical device. The driven magnet can be placed directly under a patient's skin and can be driven by an external actuation device located outside the patient's body. The external actuation device includes a driving magnet that can be placed over the driven magnet to magnetically couple the driving magnet and the driven magnet together. The driving magnet can then be rotated to rotate the driven magnet and adjust the adjustable implanted medical device. The magnetic coupling between the driven and driving magnets can be susceptible to magnetic slippage which can affect the ability of the driving magnet to properly rotate the driven magnet to lengthen the adjustable implanted medical device.

BRIEF DESCRIPTION OF THE DRAWINGS

Various embodiments will become better understood with regard to the following description, appended claims and accompanying drawings wherein:

FIG. 7 is a front cross sectional view depicting an external actuation device, in accordance with another embodiment; and FIG. 8 is a side cross sectional view of the external actuation device of FIG. 7.

DETAILED DESCRIPTION

Figure 1:
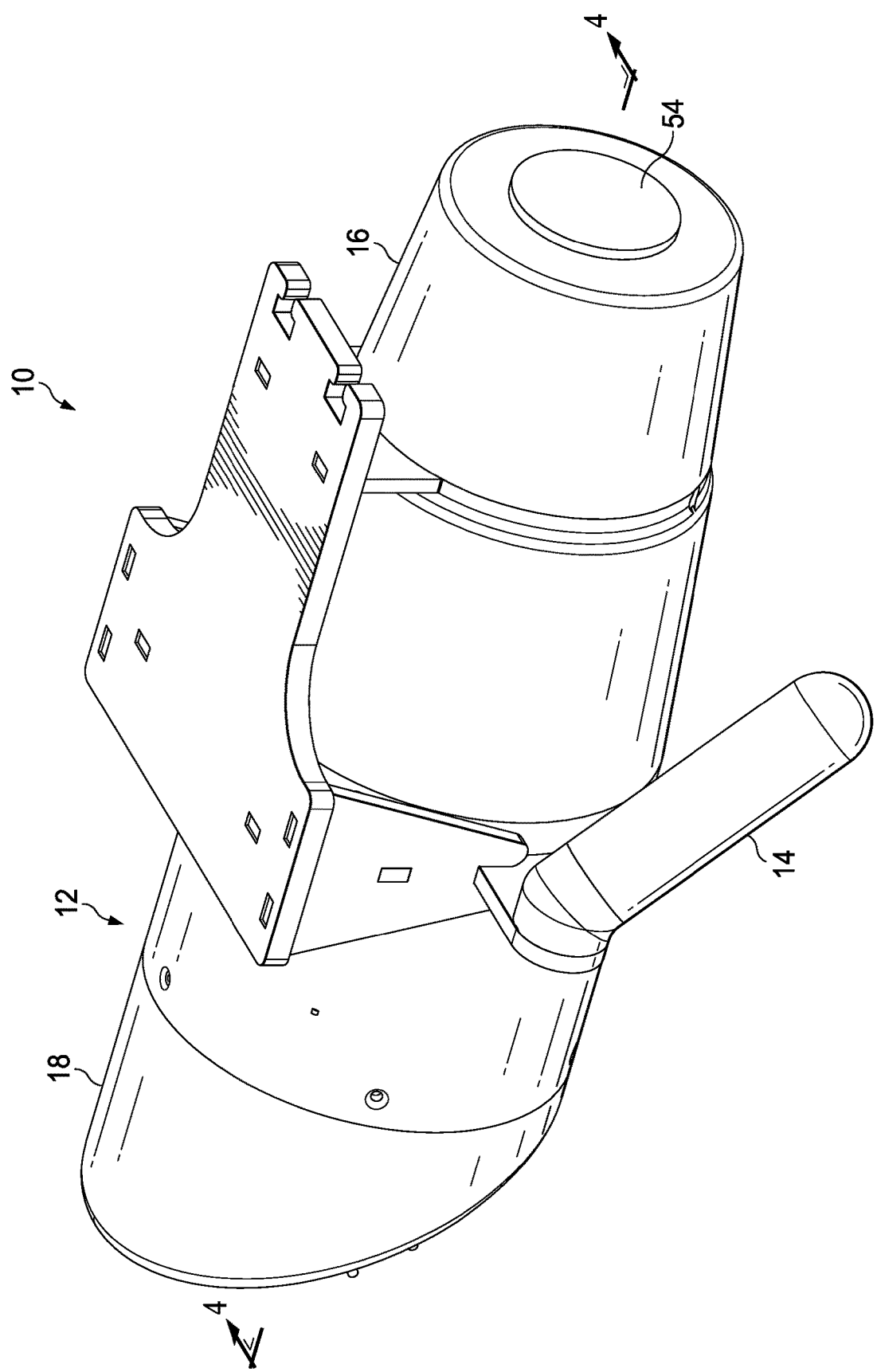
FIG. 1 is a front isometric view depicting an external actuation device, in accordance with one embodiment.
Figure 2:
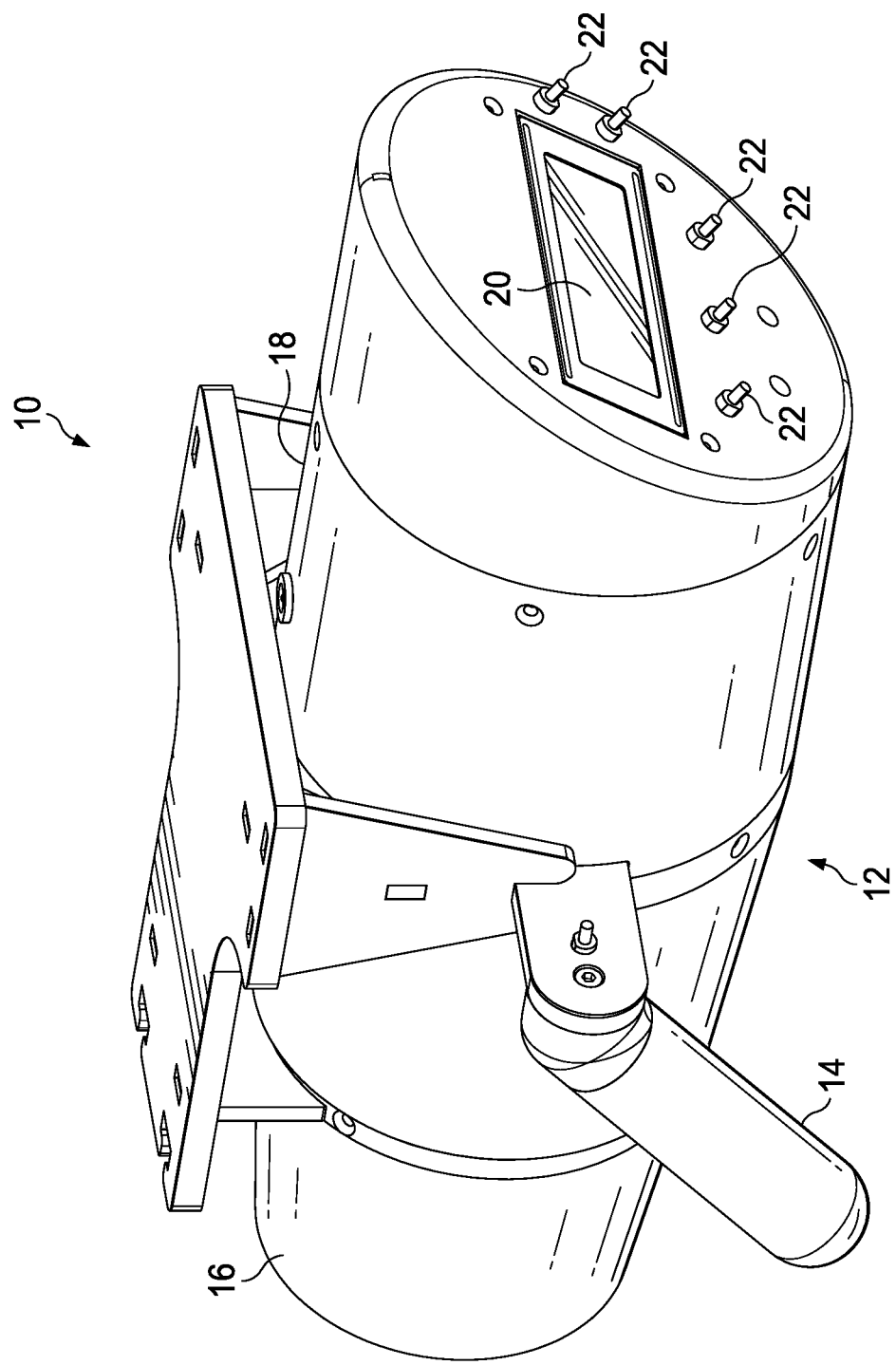
FIG. 2 is a rear isometric view of the external actuation device of FIG. 1.

Embodiments are hereinafter described in detail in connection with the views and examples of FIGS. 1-8, wherein like numbers indicate the same or corresponding elements throughout the views. An external actuation device 10 is generally depicted in FIGS. 1 and 2 and can include a housing 12 and a pair of handles 14 that are attached to the housing 12 and can be grasped by a user to facilitate manual positioning of the external actuation device 10. The housing 12 can include a front portion 16 and a rear portion 18. As illustrated in FIG. 2, a digital display 20 and a plurality of buttons 22 can be disposed on the rear portion 18 of the housing 12.

Figure 3:
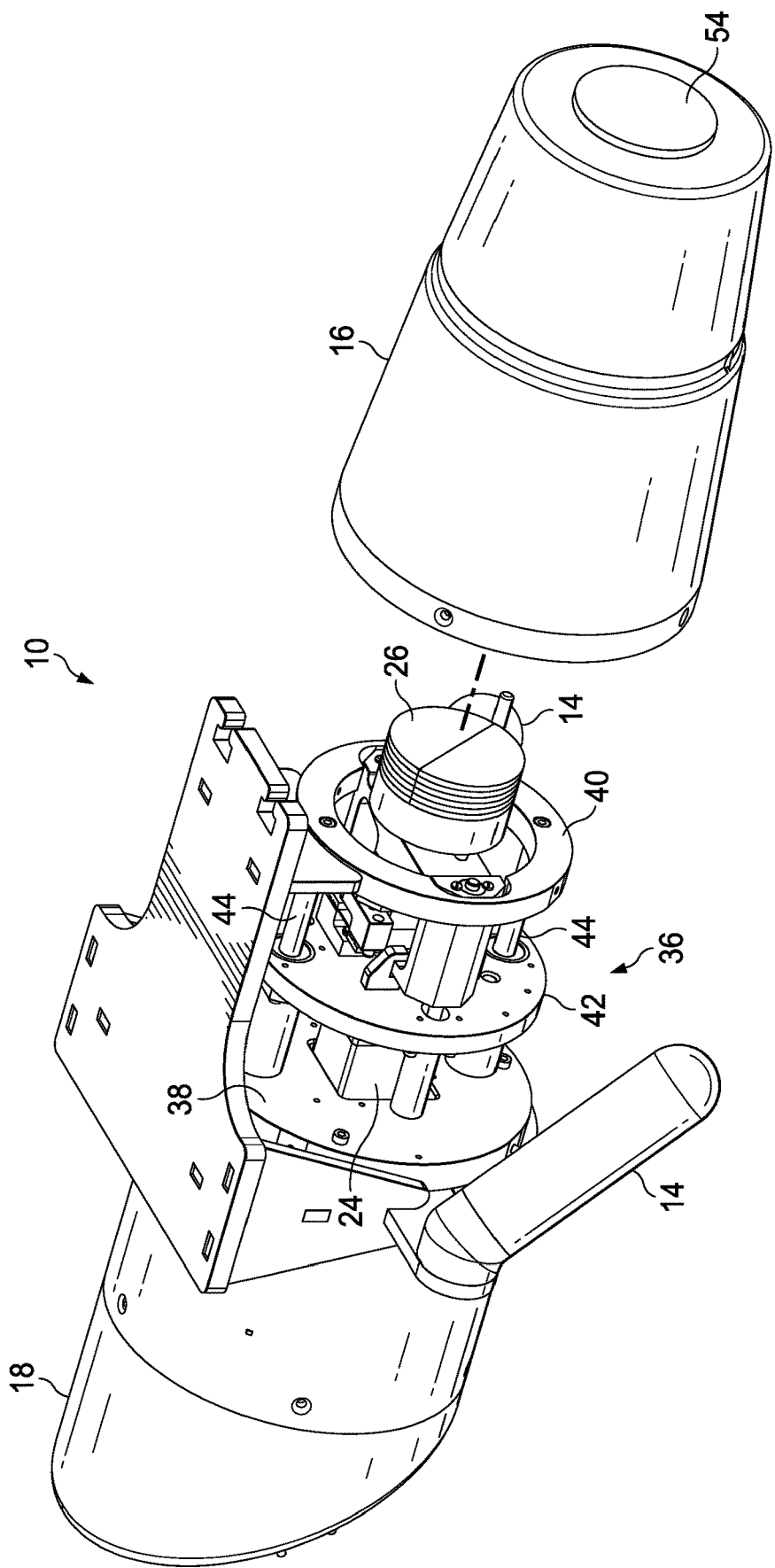
FIG. 3 is a partially exploded front isometric view of the external actuation device of FIG. 1.
Figure 4:
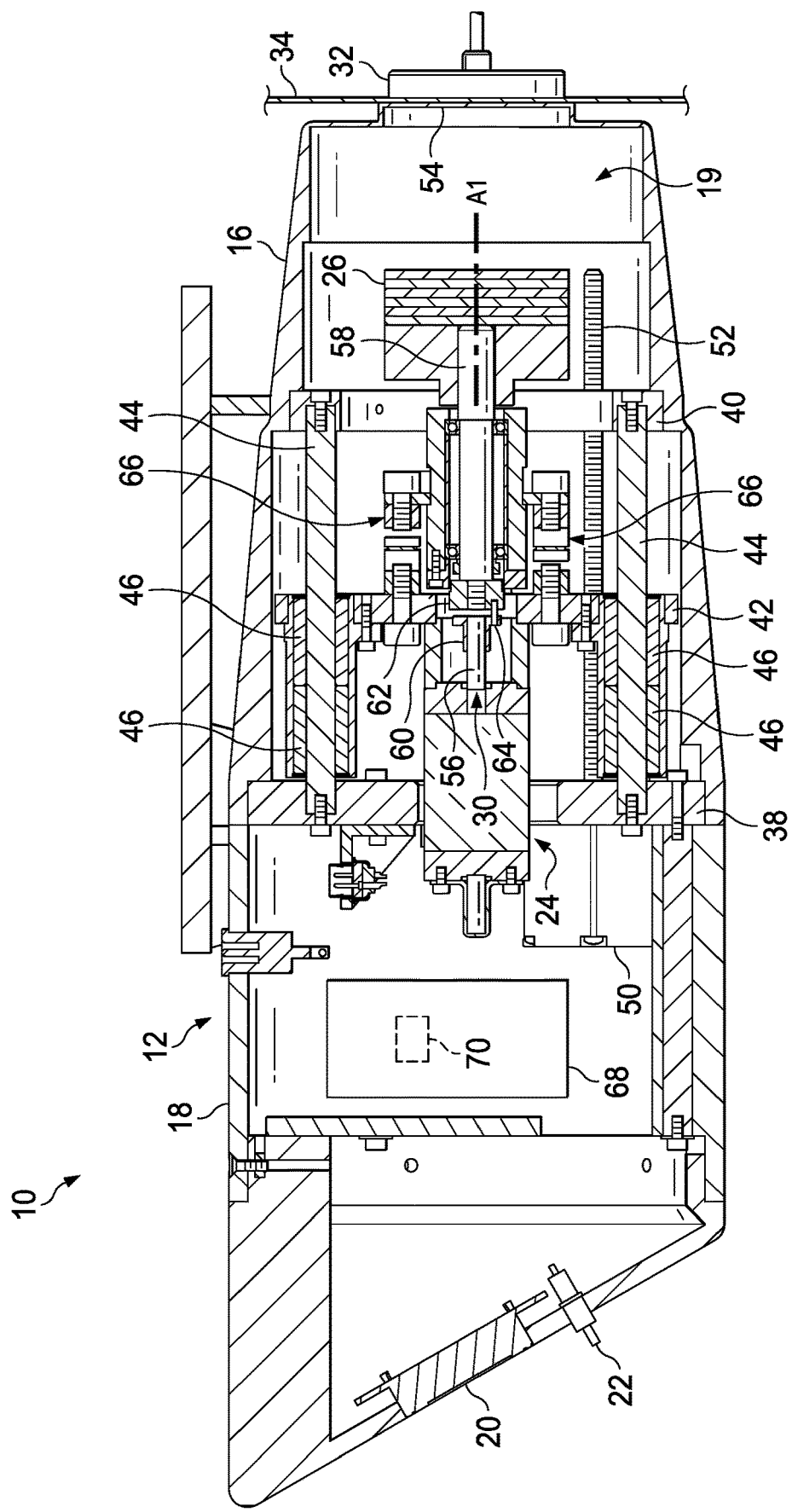
FIG. 4 is a cross sectional view taken along the line 4-4 in FIG. 1, wherein a motor and a driving magnet of the external actuation device are shown in a retracted position.

Referring now to FIGS. 3 and 4, the external actuation device 10 can include a motor 24 (FIG. 4) and a driving magnet 26 that are at least partially disposed in a receptacle 19 defined by the front portion 16. As illustrated in FIG. 4, the motor 24 can include a driveshaft 30 that is rotatable about a rotation axis A1 during operation of the motor 24. In one embodiment, the motor 24 can comprise an electric motor, but any of a variety of suitable alternative motors are contemplated, such as for example, a pneumatic motor or a hydraulic motor.

The driving magnet 26 can be rotatably coupled with the driveshaft 30 such that the driving magnet 26 is rotatable together with the driveshaft 30 about the rotation axis A1. Rotation of the driving magnet 26 can rotate a driven magnet 32 that is provided under a patient's skin 34 for non-invasively adjusting an implanted medical device (e.g., a distraction rod or a growing rod) (not shown), as will be described in further detail below. In one embodiment, the driving magnet 26 and the driven magnet 32 can each be permanent axial multipole magnets or alternatively a diametrically magnetized magnet. It is to be appreciated that although the driving magnet 26 and the driven magnet 32 are shown be disc magnets that have substantially the same diameter, any of a variety of different shapes, sizes, and or types of magnets (e.g., cylindrical magnets) can be utilized.

Still referring to FIGS. 3 and 4, the external actuation device 10 can include a frame assembly 36 that includes a rear frame member 38, a front frame member 40 and a motor mount 42. The rear and front frame members 38, 40 can be coupled together with each other via a plurality of support members 44 that extend though the motor mount 42. The housing 12 can be coupled with the rear and front frame members 38, 40. The motor 24 can be coupled with the motor mount 42.

Figure 5:
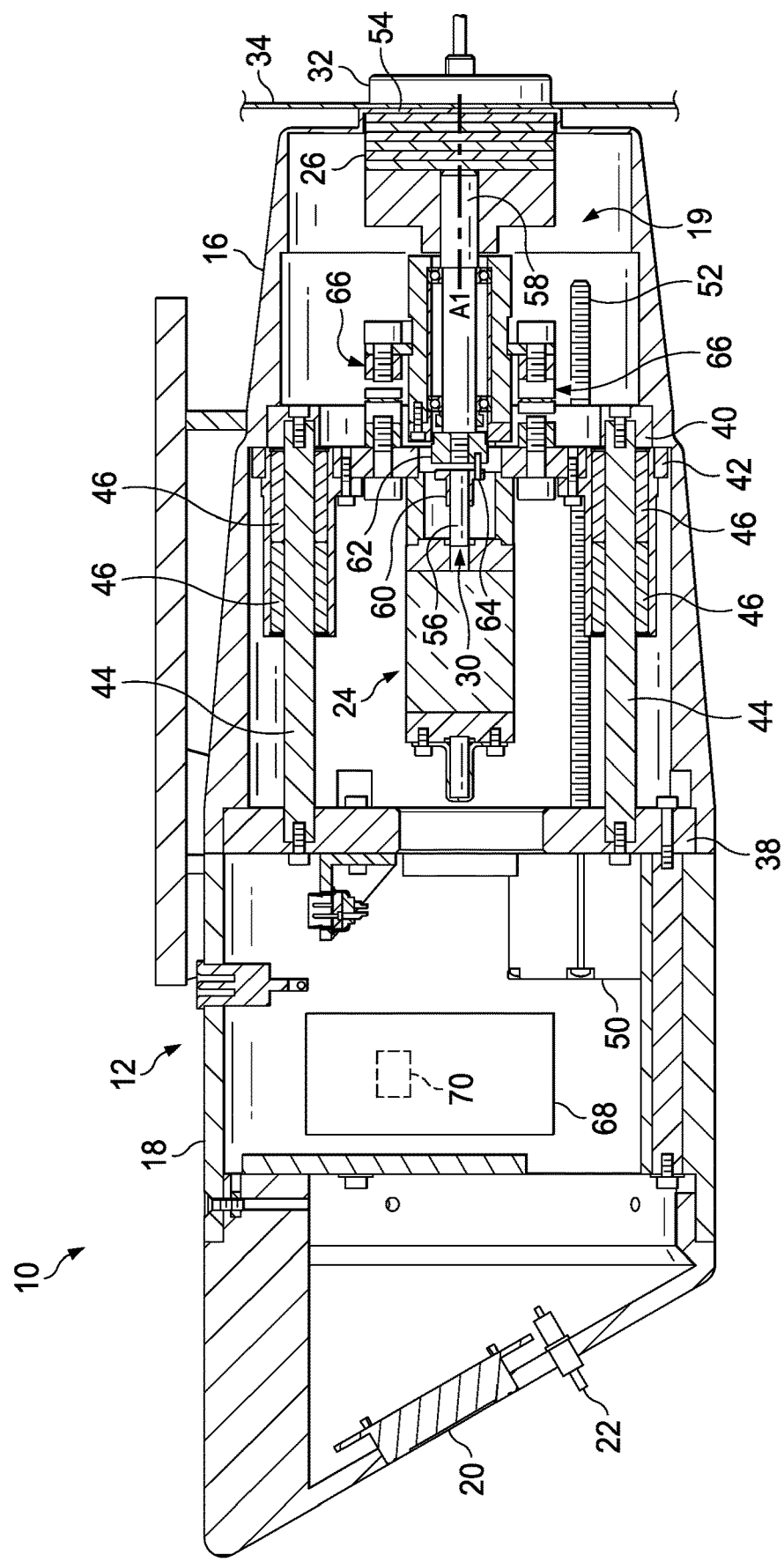
FIG. 5 is a cross sectional view of the external actuation device of FIG. 4, but with the motor and the driving magnet of the external actuation device shown in an extended position.

Referring now to FIGS. 4 and 5, the motor 24 can be slidably coupled with the housing 12 and slidable with respect to the housing 12 along the rotation axis A1 between a retracted position (FIG. 4) and an extended position (FIG. 5). To facilitate sliding of the motor 24, the motor mount 42 can be slidably coupled with the support members 44 such that the motor 24, the driving magnet 26 and the motor mount 42 are slidable together along the rotation axis A1. The motor mount 42 can include linear bearings 46 provided at the interface between the motor mount 42 and the support members 44 to facilitate sliding therebetween. It is to be appreciated that any of a variety of suitable alternative interfaces can be provided that facilitate sliding between the motor mount 42 and the support members 44.

In one embodiment, as illustrated in FIGS. 4 and 5, the external actuation device 10 can include a linear actuator 50 that facilitates powered sliding of the motor 24 and the driving magnet 26 between the retracted position (FIG. 4) and the extended position (FIG. 5). The linear actuator 50 can include a threaded shaft 52 that is threadably coupled with the motor mount 42. The threaded shaft 52 can be selectively rotated (e.g., in a clockwise and counterclockwise direction) to facilitate sliding of the motor 24 and the driving magnet 26 between the retracted position and the extended position. It is to be appreciated than any of a variety of suitable alternative actuators are contemplated that facilitate selective sliding of the motor mount 42.

When the motor 24 and the driving magnet 26 are in the retracted position, the driving magnet 26 can be spaced further from an end wall 54 of the front portion 16 of the housing 12 than when the motor 24 and the driving magnet 26 are in the extended position. When the external actuation device 10 is first placed over a patient, the motor 24 and the driving magnet 26 can initially be placed in the retracted position (FIG. 4) to prevent the driving magnet 26 from inadvertently causing the driven magnet 32 to rotate and to avoid squeezing the patient skin. Once the external actuation device 10 is positioned over the driven magnet 32, the motor 24 and the driving magnet 26 can be slid towards the extended position until there is sufficient magnetic attraction between the driving magnet 26 and the driven magnet 32 to magnetically couple the driving magnet 26 and the driven magnet 32 together. The motor 24 can then be operated to rotate the driven magnet 32 with the driving magnet 26.

The driving magnet 26 can be slidably coupled with the motor 24 such that the driving magnet 26 can slide relative to the motor 24 along the rotation axis A1. As illustrated in FIGS. 4 and 5, the driveshaft 30 can comprise a driving portion 56 and a driven portion 58. The driven portion 58 can be slidably and rotatably coupled with the driving portion 56 such that the driven portion 58 rotates together with the driving portion 56 and can slide relative to the driving portion 56. The driving portion 56 can include a driving collar 60 and the driven portion 58 can include a driven collar 62 that is spaced from the driving collar 60. The driving collar 60 and the driven collar 62 can be rotatably coupled together with a slide pin 64 that extends through each of the driving collar 60 and the driven collar 62. As such, the driving portion 56 can be powered by the motor 24 which can in turn rotate the driven portion 58 via the slide pin 64 to rotate the driving magnet 26.

The driving collar 60 and the driven collar 62 can be slidably coupled together via the slide pin 64, which can allow the driving magnet 26 to slide relative to the motor 24. When the driving magnet 26 is acted on by a magnetic force (e.g., from the driven magnet 32), the driving magnet 26 can slide towards or away from the motor 24 (e.g., via the driving collar 60 and the driven collar 62) depending on whether the magnetic force (e.g., from the driven magnet 32) is repulsive or attractive. For example, when the driving magnet 26 is magnetically coupled to the driven magnet 32, the magnetic force between the driving magnet 26 and the driven magnet 32 is attractive which causes the driving magnet 26 to slide away from the motor 24. Conversely, when the driving magnet 26 opposes the driven magnet 32 (e.g., during slip), the magnetic force between the driving magnet 26 and the driven magnet 32 is repulsive which causes the driving magnet 26 to slide towards the motor 24. It is to be appreciated that any of a variety of suitable slidable arrangements can be utilized to facilitate sliding of the driving magnet 26 with respect to the motor 24.

The distance that the driving magnet 26 slides with respect to the motor 24 (e.g., linear displacement) can be proportional to the magnetic attraction between the driving magnet 26 and the driven magnet 32. For example, the stronger the magnetic attraction is between the driving magnet 26 and the driven magnet 32, the further the driving magnet 26 slides away from the motor 24. The stronger the magnetic repulsion between the driving magnet 26 and the driven magnet 32, the further the driving magnet 26 slides towards the motor 24. The linear position of the driving magnet 26 can accordingly indicate the integrity of the magnetic coupling between the driving magnet 26 and the driven magnet 32.

As will be described in further detail below, when the external actuation device 10 is positioned on a patient and the motor 24 and the driving magnet 26 are moved towards the extended position, the linear displacement of the driving magnet 26 can indicate whether it is aligned properly with the driven magnet 32. For example, if the driving magnet 26 is aligned properly with the driven magnet 32, the magnetic attraction between the driving magnet 26 and the driven magnet 32 can cause the driving magnet 26 to slide away from the motor 24 enough to indicate that the magnetic coupling between the driving magnet 26 and the driven magnet 32 is sufficient. If the driving magnet 26 is misaligned with the driven magnet 32, the magnetic attraction between the driving magnet 26 and the driven magnet 32 isn't enough to slide the driving magnet 26 sufficiently away from the motor 24, and the driving magnet 26 must be repositioned relative to the driven magnet 32. Once the driving magnet 26 and the driven magnet 32 are properly aligned and magnetically coupled, the motor 24 is rotated to rotate the driven magnet 32. During rotation of the motor 24, the linear displacement of the driving magnet 26 can continue to be monitored to determine whether the driving magnet 26 and the driven magnet 32 inadvertently slip.

Still referring to FIGS. 4 and 5, the external actuation device 10 can comprise a strain gage 66 that is mounted to the motor mount 42. The strain gage 66 can be configured to detect the linear displacement of the driving magnet 26 (e.g., the linear displacement between the driving collar 60 and the driven collar 62) as a function of the position of the driveshaft 30 relative to the motor mount 42. When no external forces acts on the driving magnet 26 such as, for example, when the motor 24 and the driving magnet 26 are in the retracted positon, the driving magnet 26 is at a neutral position with respect to the motor 24 such that the strain gage 66 is not bent and thus detects no force. When the driving magnet 26 is acted on by a magnetic force (e.g., from the driven magnet 32), the driving magnet 26 can slide towards or away from the motor 24 (e.g., via the driving collar 60 and the driven collar 62) in proportional response to a repulsive or attractive magnetic force (e.g., from the driven magnet 32). For example, when the driving magnet 26 is magnetically coupled to the driven magnet 32, the magnetic force acting on the driving magnet causes the driving magnet 26 to move away from the motor 24 thus bending the strain gauge 66 proportionally to the force. Conversely, when the driving magnet 26 is repulsed from the driven magnet 32 (e.g., during slip between the driving magnet 26 and driven magnet 32), the magnetic force between the driving magnet 26 and the driven magnet 32 can slide the driving magnet 26 towards the motor 24 which can bend the strain gauge 66 in the opposite direction and proportional to the repulsive magnetic force. The strain gage 66 can facilitate biasing of the driving magnet 26 into the neutral position such that when the magnetic force is removed from the driving magnet 26 it automatically returns to the neutral position. It is to be appreciated that any of a variety or quantity of suitable alternative sensors are contemplated and can be placed at any of a variety of locations along the external actuation device 10 to facilitate detection of a magnetic force between the driving magnet 26 and the driven magnet 32. In one example, a linear displacement sensor can be provided at the driving magnet 26 such that its linear position is detected directly. In another example, a linear encoder can be provided that is configured to detect a plurality of discrete linear displacement positions of the driving magnet 26. In yet another example, a force sensor can be provided. It is also to be appreciated that any of a variety of suitable alternative biasing members can be used for biasing the driving magnet 26 towards the neutral position, such as, for example, a spring or an elastomeric member.

To differentiate between a magnetic force and a gravitational force acting on the driving magnet 26, an accelerometer 67 controller to determine the orientation of the device. For example, if the device is held vertically above the patient, weight of the driving magnet 26 acts on the strain gauge 66 and should be subtracted from the measured force to ensure that only the magnetic force is measured. Conversely, if the device is perfectly horizontal, gravitational force has no effect on the measurement.

The external actuation device 10 can include a controller 68 that is in communication with the motor 24, the linear actuator 50, and the strain gage 66. The controller 68 can be configured to facilitate selective operation of the motor 24 based upon the magnetic force imparted on the driving magnet 26. When the external actuation device 10 is positioned on a patient and the driving magnet 26 is slid from the retracted position (FIG. 4) to the extended position (FIG. 5), the controller 68 can measure the attractive force between the driving magnet 26 and the driven magnet 32 as a function of the linear position of the driving magnet 26 detected from the strain gage 66. Once the attractive force reaches a predefined threshold (e.g., between about 0.1 N and about 100 N and preferably between about 1 Nm and about 3 Nm), the controller 68 can stop the linear actuator 50 to prevent further sliding of the driving magnet 26 into the extended position. The controller 68 can then facilitate operation of the motor 24 to rotate the driven magnet 32. In one embodiment, the motor 24 can comprise a stepper motor that is configured to rotate a precise amount (e.g., defined by a user) based on a command produced by the controller 68. The driving magnet 26 can accordingly be rotated a precise amount such that an associated adjustable implant device can be precisely adjusted via the driven magnet 32.

During rotation of the motor 24, the controller 68 can measure the integrity of the attractive force between the driving magnet 26 and the driven magnet 32 as a function of the linear position of the driving magnet 26 detected from the strain gage 66. If the driving magnet 26 and the driven magnet 32 begin to slip (e.g., when the torque required to rotate the driven magnet 32 increases), the north/south poles of the driving magnet 26 can begin to align with the north/south poles of the driven magnet 32 which can cause the driving magnet 26 to be temporarily linearly displaced upwardly. If the driving magnet 26 moves far enough upwardly to significantly disrupt the magnetic coupling between the driven magnet 32 and the driving magnet 26 (as detected from the strain gage 66), the controller 68 can deactivate the motor 24 and can issue an audible or visual warning to a user that a problem might exist. In one embodiment, the controller 68 can compare the linear displacement of the driving magnet 26 to a predefined threshold value that represents the point at which the magnetic coupling becomes unstable.

To differentiate between a magnetic force and a gravitational force acting on the driving magnet 26, the controller 68 can include an accelerometer 70 that facilitates determination of the orientation of the external actuation device 10. The controller 68 can account for the orientation of the external actuation device 10 when determining the magnetic force being applied to the driving magnet 26. For example, if the external actuation device 10 is held vertically above the patient, the weight of the driving magnet 26 can act on the strain gauge 66 and the controller 68 can subtract the weight of the driving magnet 26 from the measured force to ensure that only the magnetic force is measured. Conversely, if the device is perfectly horizontal, gravitational force has no effect on the measurement and the controller 68.

It is to be appreciated that during sliding of the driving magnet 26 between the retracted position (FIG. 4) to the extended position (FIG. 5), the attractive force between the driving magnet 26 and the driven magnet 32 detected by the controller 68 never reaches the predefined threshold, the controller 68 can stop the linear actuator 50 once the driving magnet 26 reaches the extended position and can issue an alert to the user that the external actuation device 10 may need to be repositioned.

The controller 68 can also be in communication with the digital display 20 and the plurality of buttons 22. The controller 68 can be configured to facilitate the presentation of certain operating information to a user on the digital display 20 as will be described in further detail below. A user can use the buttons 22 to control the operation of the external actuation device as will be described in further detail below.

It is to be appreciated that although the digital display 20, the buttons 22, and the controller 68 are shown to be provided on-board the external actuation device 10, the external actuation device 10 can additionally or alternatively be controlled from a remote computing device (not shown), such as a handheld remote or a smartphone, via a wired or wireless connection. It is also to be appreciated that the external actuation device 10 can be electrically powered from an external power source (e.g., from an electrical wall outlet) and/or from an onboard power storage device, such as a battery.

Figure 6:
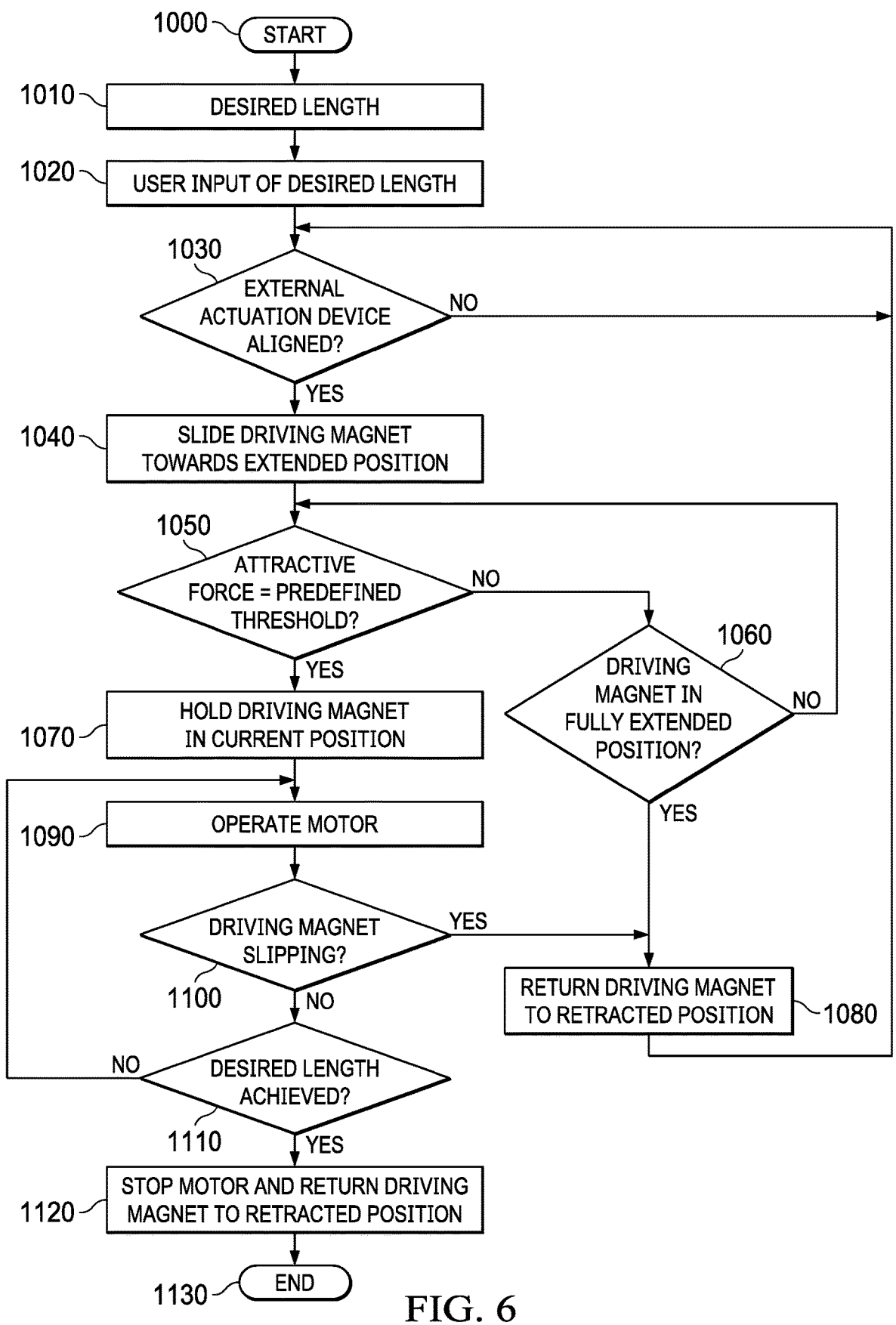
FIG. 6 is a flow chart depicting a control routine implemented by the controller of FIG. 4, in accordance with one embodiment.

One embodiment of a control routine implemented by the controller 68 during operation of the external actuation device 10 is generally illustrated in FIG. 6. Upon startup (1000), the controller 68 can query the user to input the desired length that the adjustable implanted medical device is to be extended (1010). The user can input the amount of desired distance in the controller 68 via the buttons 22 (1020). The controller 68 can then prompt the user on the digital display 20 to confirm that the external actuation device 10 has been aligned over the driven magnet 32 (1030). Once the user confirms alignment of the external actuation device 10 using the buttons 22, the controller 68 can facilitate sliding of the motor 24 and the driving magnet 26 from the retracted position to the extended position (1040). During sliding of the motor 24 and the driving magnet 26 towards the extended position, the controller 68 can determine whether the attractive force between the driving magnet 26 and the driven magnet 32 (via the strain gage 66) has reached a predefined threshold (1050). In one embodiment, the predefined threshold can be between about 0.1 N and about 100 N and preferably between about 1 Nm and about 3 Nm. In some embodiments, the predefined threshold can be selected by a user (via the digital display 20 and the buttons 22). In other embodiments, the predefined threshold can be preset (e.g., from the manufacturer). If the attractive force reaches the predefined threshold before the motor 24 and the driving magnet 26 reach the extended position (1060), the controller 68 can stop the linear actuator 50 to hold the current position of the motor 24 and the driving magnet 26 (1070). If the motor 24 and the driving magnet 26 reach the extended position before the attractive force reaches the predefined threshold, the motor 24 and the driving magnet 26 can be returned to the retracted position (1080) and the controller 68 can prompt the user again to align the external actuation device 10 over the driven magnet 32 (1030).

Returning to step (1070), after the current position of the motor 24 and the driving magnet 26 is held, the motor 24 can be operated to rotate the driven magnet (1090). During rotation of the motor 24, the controller 68 can determine (e.g., from the strain gage 66) whether the driving magnet 26 and the driven magnet 32 are slipping (1100). If the driving magnet 26 and the driven magnet 32 are slipping, the motor 24 is stopped and the driving magnet 26 can be returned to the retracted position (1080) and the controller 68 can prompt the user again to align the external actuation device 10 over the driven magnet 32 (1030) to start the process again. If the driving magnet 26 and the driven magnet 32 are not slipping, the controller 68 can continue to operate the motor 24 until the selected distance for the adjustable implanted medical device is reached (1110). Once the selected distance for the adjustable implanted medical device is achieved, the controller 68 can stop the motor 24 and can return the driving magnet 26 to the retracted position (1120) which can end the control routine (1130).

An alternative embodiment of an external actuation device 110 is illustrated in FIGS. 7 and 8 and can be similar to, or the same in many respects as, the external actuation device 10 illustrated in FIGS. 1-5. For example, the external actuation device 110 can comprise a housing 112 and a motor 124 that is coupled with a motor mount 142. A driving magnet 126 can be coupled with a driveshaft 130 of the motor 124. A linear displacement sensor 166 can be provided to detect the linear position of the driving magnet 126 as a function of the linear position of the motor mount 142. The motor mount 142 can be coupled with the housing 112 by an elastomeric structure 161 or another otherwise flexible structure. When the driving magnet 126 is provided over a driven magnet 132, the elastomeric structure 161 can flex to allow for measuring of the magnetic force acting on the driving magnet via the linear displacement sensor 166.

It can be appreciated that the processes associated with the present embodiments may be executed by a controller 68 or other programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A non-transitory computer-readable medium may also include memory storage that may be physical, virtual, permanent, temporary, semi-permanent and/or semi-temporary.

A "controller" or "processor" may be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein may include memory for storing certain software applications used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable memory media.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present disclosure based on the description herein with only a reasonable effort and without undue experimentation.

In various embodiments, the systems and methods described herein may be configured and/or programmed to include one or more of the above-described electronic, computer-based elements and components. In addition, these elements and components may be particularly configured to execute the various rules, algorithms, programs, processes, and method steps described herein.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather, it is hereby intended that the scope be defined by the claims appended hereto. Also, for any methods claimed and/or described, regardless of whether the method is described in conjunction with a flow diagram, it should be understood that unless otherwise specified or required by context, any explicit or implicit ordering of steps performed in the execution of a method does not imply that those steps must be performed in the order presented and may be performed in a different order or in parallel.

What is claimed is:

1. An external actuation device comprising:
   a housing;
   a motor comprising a driveshaft that is rotatable about a rotation axis;
   a driving magnet rotatably coupled with the driveshaft and rotatable together with the driveshaft about the rotation axis;
   a sensor associated with the driving magnet and configured to facilitate detection of a magnetic force imparted to the driving magnet; and
   a controller in communication with the motor and the sensor, the controller being configured to facilitate selective operation of the motor based upon the magnetic force detected by the sensor, wherein:
      the driving magnet is slidably coupled with the driveshaft such that the driving magnet slides relative to the motor along the rotation axis; and
      the sensor is configured to facilitate detection of the magnetic force as a function of linear displacement of the driving magnet relative to the motor.

2. The external actuation device of claim 1 wherein the sensor comprises a strain gauge.

3. The external actuation device of claim 1 wherein the driving magnet comprises one or more of an axial multipole magnet and a diametrically magnetized permanent magnet.

4. The external actuation device of claim 1 wherein the motor comprises a stepper motor.

5. The external actuation device of claim 4 wherein:
   the controller is configured to operate the stepper motor with a command signal; and
   the controller is configured to detect a rotational position of the driving magnet based upon the command signal from the controller.

6. An external actuation device comprising:
   a housing;
   a motor comprising a driveshaft that is rotatable about a rotation axis;
   a driving magnet rotatably coupled with the driveshaft and rotatable together with the driveshaft about the rotation axis;
   a sensor associated with the driving magnet and configured to facilitate detection of a magnetic force imparted to the driving magnet; and
   a controller in communication with the motor and the sensor, the controller being configured to facilitate selective operation of the motor based upon the magnetic force detected by the sensor, wherein:
      the driveshaft comprises a driving portion and a driven portion;
      the driven portion is rotatably coupled with the driving portion such that the driven portion rotates together with the driving portion; and
      the driven portion is slidably coupled with the driving portion such that the driven portion slides relative to the driving portion.

7. The external actuation device of claim 6 further comprising a slide pin that facilitates rotatable and slidable coupling of the driving portion and the driven portion together.

8. The external actuation device of claim 7 wherein:
   the driving portion comprises a driving collar;
   the driven portion comprises a driven collar that is spaced from the driving collar; and
   the slide pin extends between each of the driving collar and the driven collar to facilitate rotatable and slidable coupling therebetween.

9. An external actuation device comprising:
   a housing;
   a motor comprising a driveshaft that is rotatable about a rotation axis;
   a driving magnet rotatably coupled with the driveshaft and rotatable together with the driveshaft about the rotation axis, the driving magnet being slidably coupled with the housing and slidable along the rotation axis relative to the housing between a retracted position and an extended position;
   a sensor associated with the driving magnet and configured to detect a magnetic force between the driving magnet and a driven magnet disposed adjacent to the driving magnet; and
   a controller in communication with the motor and the sensor, the controller being configured to facilitate selective operation of the motor based upon the magnetic force detected by the sensor.

10. The external actuation device of claim 9 wherein the motor and the driving magnet are slidable together relative to the housing between the retracted position and the extended position.

11. The external actuation device of claim 10 wherein:
    the driving magnet is slidably coupled with the driveshaft and is configured to slide relative to the motor; and
    the sensor is configured to facilitate detection of a magnetic force imparted to the driving magnet as a function of linear displacement of the driving magnet relative to the motor.

12. The external actuation device of claim 11 wherein the sensor comprises a strain gauge.

13. The external actuation device of claim 9 wherein the driving magnet comprises one or more of an axial multipole magnet and a diametrically magnetized permanent magnet.

14. The external actuation device of claim 9 further comprising an actuator that facilitates sliding of the driving magnet between the retracted position and the extended position.

15. The external actuation device of claim 14 wherein the controller is in communication with the actuator and is configured to facilitate selective operation of the actuator based upon the magnetic force detected by the sensor.

16. The external actuation device of claim 14 wherein the controller is configured to cease operation of the actuator once a predefined magnetic force is achieved between the driving magnet and the driven magnet.

17. The external actuation device of claim 9 wherein the motor comprises a stepper motor.

18. The external actuation device of claim 17 wherein:
    the controller is configured to operate the stepper motor with a command signal; and
    the controller is configured to detect a rotational position of the driving magnet based upon the command signal from the controller.

19. An external actuation device comprising:
    a housing;
    a motor comprising a driveshaft that is rotatable about a rotation axis, the motor being slidably coupled with the housing and slidable along the rotation axis relative to the housing between a retracted position and an extended position, wherein the driveshaft comprises:
       a driving portion that comprises a driving collar;
       a driven portion that comprises a driven collar that is spaced from the driving collar; and
       a slide pin that extends between each of the driving collar and the driven collar to facilitate rotatable and slidable coupling therebetween;

a driving magnet rotatably coupled with the driveshaft and rotatable together with the driveshaft about the rotation axis, the driving magnet being slidably coupled with the driveshaft such that the driving magnet slides relative to the motor along the rotation axis;

a sensor associated with the driving magnet and configured to facilitate detection of a magnetic force imparted to the driving magnet as a function of linear displacement of the driving magnet relative to the motor; and a controller in communication with the motor and the sensor, the controller being configured to facilitate selective operation of the motor based upon the magnetic force detected by the sensor, wherein the driving collar and the driven collar each comprise complementary magnets that are in equilibrium with each other such that the driving collar and the driven collar are held in a spaced relationship relative to each other when a magnetic force is not imparted to the driving magnet.

* * * * *